United States Patent [19]

Reynard

[11] Patent Number: 5,651,783
[45] Date of Patent: *Jul. 29, 1997

[54] FIBER OPTIC SLEEVE FOR SURGICAL INSTRUMENTS

[76] Inventor: Michael Reynard, 1301 20th St., #260, Santa Monica, Calif. 90404

[*] Notice: The term of this patent shall not extend beyond the expiration date of Pat. No. 5,478,338.

[21] Appl. No.: 575,829

[22] Filed: Dec. 20, 1995

[51] Int. Cl.$^6$ ............................ A61B 17/36
[52] U.S. Cl. ............................ 606/4; 606/17
[58] Field of Search ............... 606/10, 11, 12, 606/14, 15, 16, 17; 607/88, 89

[56] References Cited

U.S. PATENT DOCUMENTS 5,257,991  11/1993  Fletcher et al. .................... 606/17
5,431,646   7/1995  Vassiliadis et al. ................ 606/17
5,478,338  12/1995  Reynard ............................ 606/15
5,496,308   3/1996  Brown et al. ...................... 606/17

*Primary Examiner*—Angela D. Sykes
*Assistant Examiner*—Sonya Harris-Ogugua
*Attorney, Agent, or Firm*—Willie Krawitz

[57] ABSTRACT

A fiber optic integrated phacoemulsification system is disclosed comprising surgical handpieces for cataract surgery which incorporate fiber optic bundles that transmit visible light to enhance visualization by intraocular illumination. Patient safety is improved by the oblique lighting to the retina, thereby reducing the necessity of direct coaxial light from the surgical microscope. The fiber optic bundles enable the application of laser energy or visible light and permit endoscope visualization of intraocular structures either through the surgical handpiece or through an end piece attachment.

22 Claims, 4 Drawing Sheets

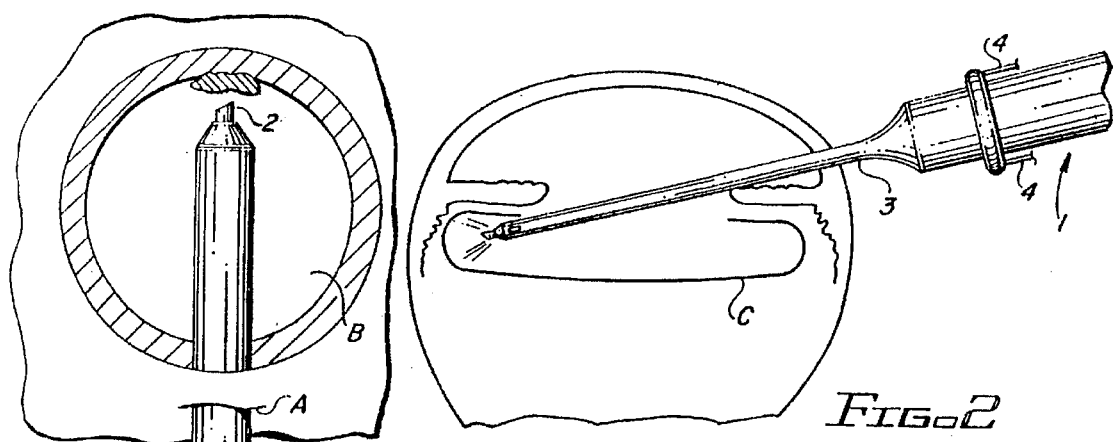
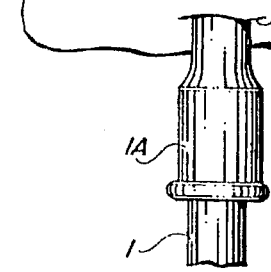
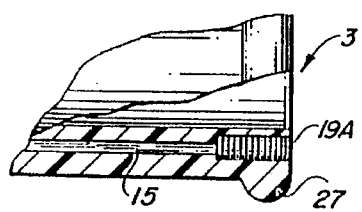
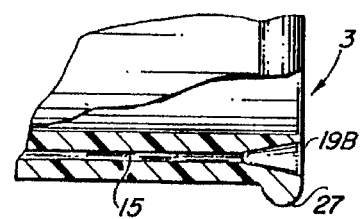
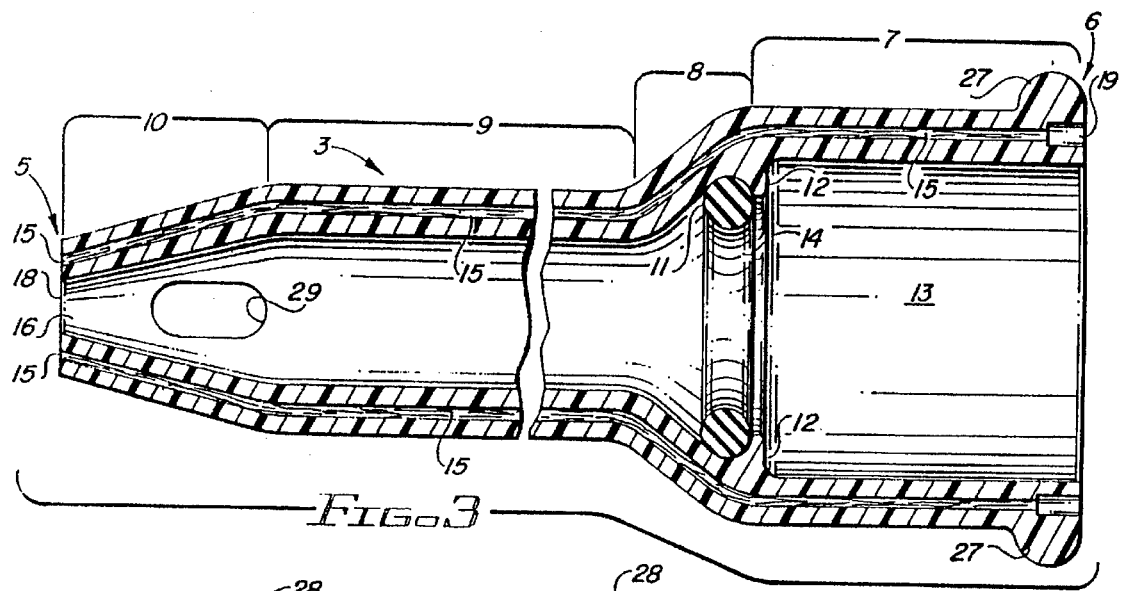
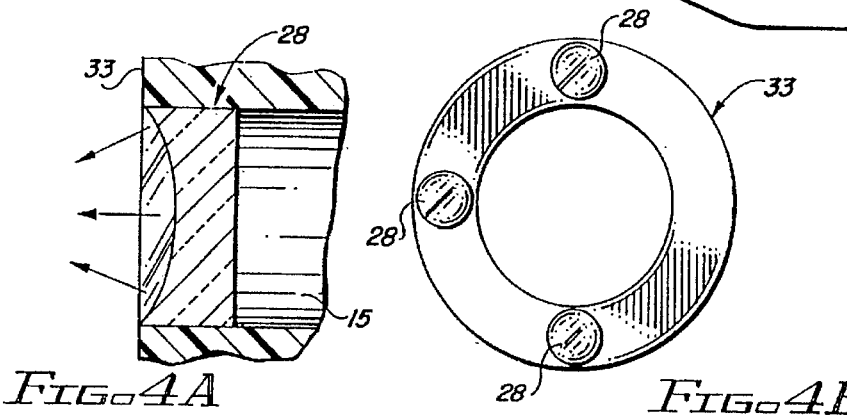

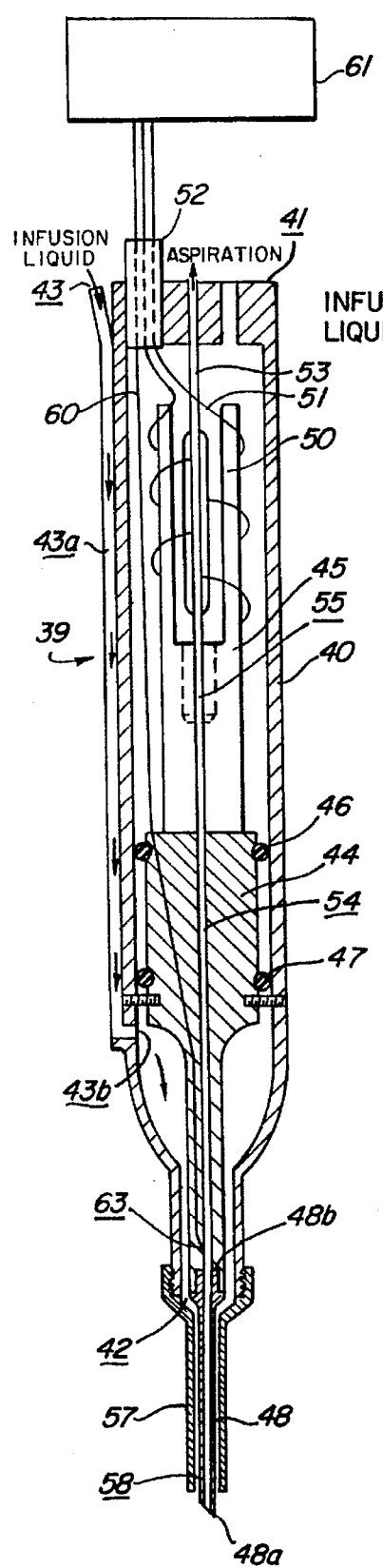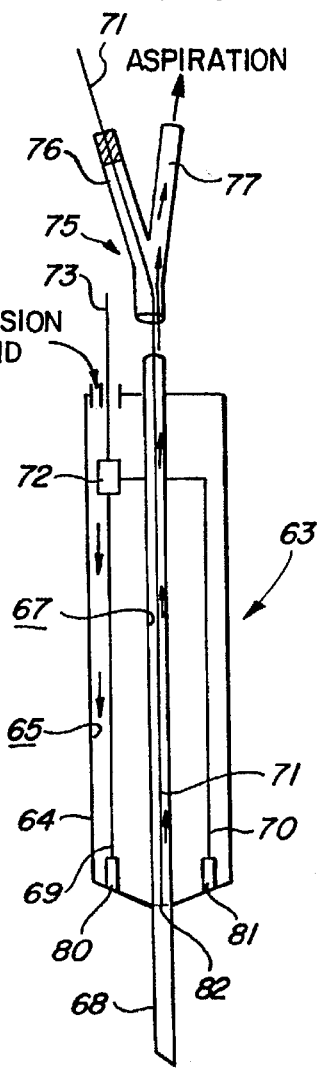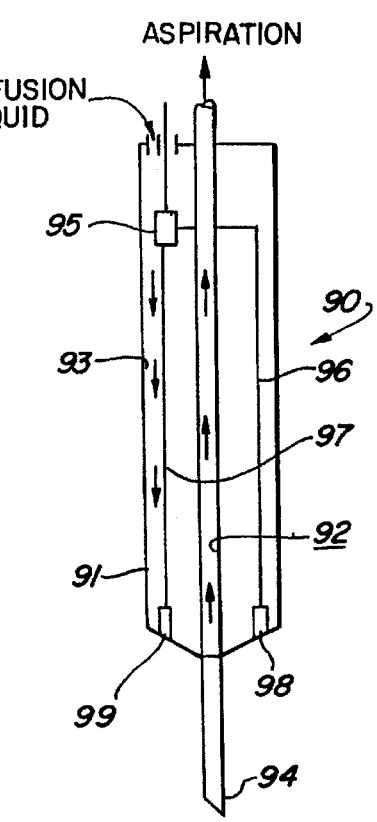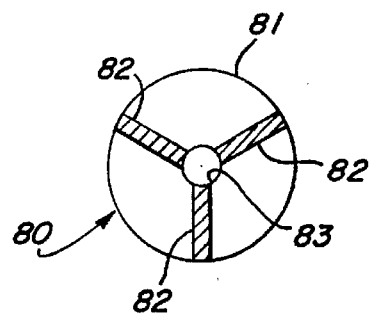

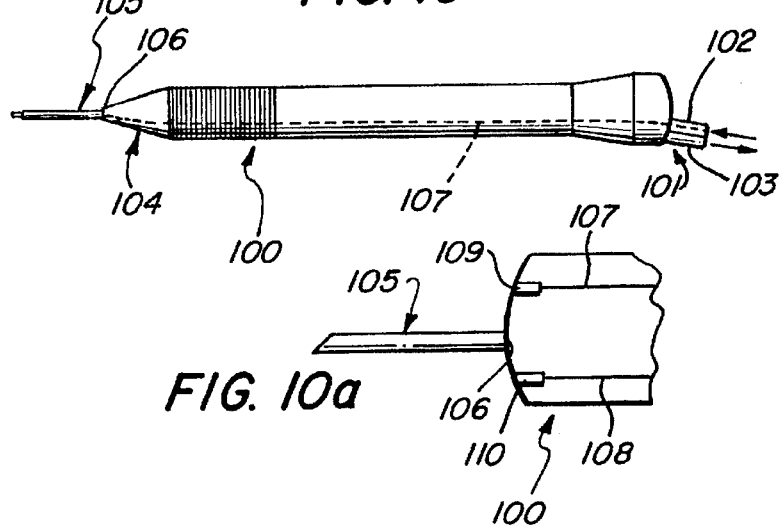
FIG. 10
FIG. 10a
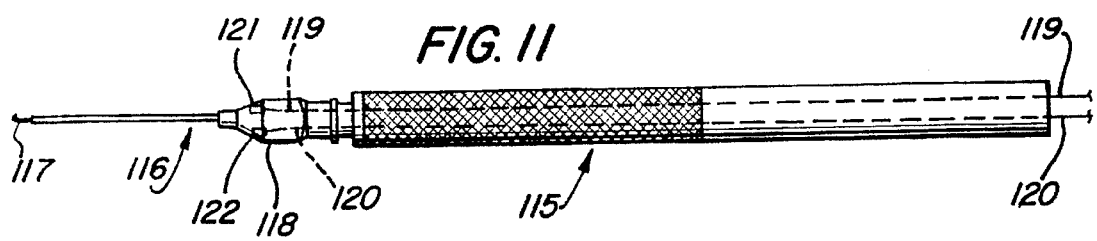
FIG. 11
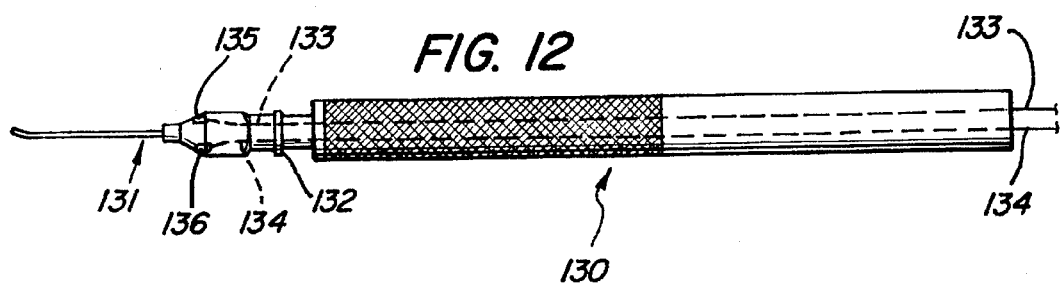
FIG. 12
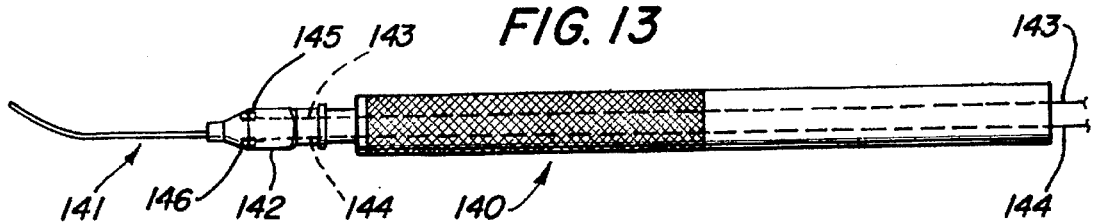
FIG. 13

FIBER OPTIC SLEEVE FOR SURGICAL INSTRUMENTS

BACKGROUND OF THE INVENTION

1. Field of the Invention

This invention relates to surgical devices and, more particularly, to devices for effecting the transmission of light for endoillumination, intraocular endoscopy, or laser application to intraocular tissue.

2. Discussion of the Related Art

The most widely accepted prior art means for performing intraocular surgery in the anterior segment of the eye comprise a variety of instruments designed for irrigation, ablation, cutting and removal of tissue. Separate instruments for irrigation, illumination and laser application are known, but they have the disadvantage of requiring multiple surgical openings in the eye and may be cumbersome to operate for the surgeon. Multiple surgical openings in the eye and multiple surgical instruments add to the risk of complications and increase the difficulty of the surgical procedure. Surgical instruments that combine water infusion, suction and light conducting elements in a single probe have been described, but they have the inherent physical limitations imposed by side-by-side conducting channels. Another problem that arises in the use of complex multiple-element surgical instruments is the cost and labor of repeated sterilization.

Examples of ophthalmic instruments of the type described are commercially available from Grieshaber & Co., Inc., 3000 Cabot Boulevard West, Langhorne, Pa. 19047. These are shown in company brochures under the title "The Grieshaber Light Source and Family of Accessories".

Recent reports of specific cases in which prior art instruments of the type described are used may be found in *Arch Ophthalmol* Vol. 111, Jul. 1993: "Neodymium-YAG Laser Phacolysis of the Human Cataractous Lens" and *Ophthalmology*, Vol. 100, Number 7, Jul. 1993: "Experimental Endoscopic Goniotomy". The former describes a performance of Nd-YAG laser phacolysis on a particular patient for the removal of a nuclear sclerotic cataract. The latter report describes the use of an endoscope coupled to another surgical instrument in experimental surgery on porcine cadaver eyes designed to lead to the use of a tiny endoscope attached to a goniotomy needle for the treatment of primary infantile glaucoma. Both of these arrangements are subject to the deficiencies described hereinabove.

OBJECTS OF THE INVENTION

The primary object of the present invention is to provide an attachment for surgical devices, specifically adaptable for intraocular surgery, that provides illumination, endoendoscopy, and a means for laser beam delivery. The device is economical in its construction so as to be inexpensively re-sterilized and reused or simply discarded after each use because of its low cost. The device comprises a fiber optic sleeve which is easily and inexpensively fabricated and useful in conjunction with a variety of surgical procedures. For purposes of illustration, arrangements of the invention will be discussed in relation to a preferred embodiment for ophthalmic use and with respect to various considerations involved in the recommended utilization of the arrangements disclosed herein. The invention is not so limited, however, and it is entitled to the scope of protection afforded by the accompanying claims.

Illumination.

The vast majority of intraocular surgical procedures involve visualization by the surgeon through a high-powered microscope using intense coaxial illumination. It is well-documented that direct and intense microscope illumination may be damaging to the retina; macular edema with corresponding reduction of vision is the primary side effect. As an alternative, focal illumination directed at an oblique angle and in a direction away from the retina can enable the surgeon to reduce the amount of direct microscope light necessary to perform ocular surgery, thereby minimizing potential retinal light toxicity.

A common problem in the present state of the art is that visualization of the proximal tip of the surgical device is often impeded when blood, scar tissue, or inflammatory debris is present. During normal phacoemulsification of a cataract in the presence of a small pupil, the proximal tip of the surgical device is obscured behind the iris. Consequently, there is a higher risk of inadvertent rupture of the lens capsule, vitreous prolapse into the anterior chamber and retinal problems, all of which are associated with visual loss. Use of a fiber optic sleeve in accordance with the invention permits visualization of the anterior portion of the surgical instrument by virtue of transillumination through the iris leaf or opaque media. Moreover, it is often difficult for the operating surgeon to judge the depth of cataract or other intraocular structures. Surgical intervention to an excessive depth can lead to complications resulting in visual loss. Focal illumination at an oblique angle with a fiber optic sleeve of the invention can enhance the operating surgeon's ability to judge the depth of intraocular structures and thereby lessen the possibility of surgical mishap.

Endoscopy.

Direct visualization of vital intraocular structures during surgery can be realized with the image-carrying capacity of the fiber optic sleeve of the invention. Intraocular microendoscopy can be utilized to confirm positioning of haptics of a posterior chamber intraocular lens. At present, the surgeon is not able to visually inspect and confirm the location of posterior chamber intraocular lens haptics. Malpositioned haptics may result in lens decentration subsequent to surgery. Decentration of lens implants causing visual loss or distortion necessitates corrective surgical procedures. Visualization of intraocular lens haptics in combination with positioning adjustments at the time of surgery can prevent intraocular lens decentration.

Laser Application.

Finally, the fiber optic sleeve of my invention permits application of laser illumination for intraocular tissue coagulation and ablation. The present invention provides a means to couple laser energy delivery with simultaneous illumination and visualization. Lasers capable of transmission through the fiber optic sleeve include Holmium:YAG (2.1 um wavelength), Thulium:YAG (1.96 um wavelength), Erbium:YAG (2.94 um wavelength), Hydrogen Fluoride (2.7–3.0 um wavelength), Deuterium Fluoride (3.7–4.1 um wavelength), Carbon Monoxide (5.3–5.7 um wavelength), Carbon Dioxide (10.6 um wavelength), Argon Fluoride (193 nm wavelength), Krypton Fluoride (248 nm wavelength), Diode Red (670 nm wavelength), Xenon Chloride (308 nm wavelength), Argon Blue (488 nm wavelength), and Argon Green (514 nm wavelength).

Laser ablation of ciliary body processes responsible for producing excessive intraocular fluid, and for creation of a drainage fistula through the sclera, permits control of elevated intraocular pressure and glaucoma. Laser photocoagulation of ciliary body processes for treatment of glaucoma used in the present art involves external treatment through peripheral iridectomies. The effectiveness of this treatment is significantly limited because only a small number of ciliary processes can be treated. In the presently preferred embodiment, the endolaser and endoscopic capabilities permit treatment of the ciliary processes for at least 180 degrees, allowing for an enhanced laser therapeutic effect.

Manual methods used for anterior lens capsulotomy have inherent disadvantages that includes inadvertent radial capsule tears. Significant radial capsule tears are likely to result in complications such as vitreous prolapse or implant subluxation. Such disturbances can reduce or eliminate the visual benefit of an eye operation, or delay the healing process. Anterior Capsulotomy with laser allows for controlled and precision capsulotomy edges unattainable by manual methods.

In addition laser application through the fiber optic sleeve is useful as a substitute or adjunct for ultrasonic phacoemulsification in cataract surgery.

In summary, from the foregoing discussion it will be appreciated that the fiber optic sleeve of the present invention is particularly beneficial when used with implements for intraocular surgery. It is of simple and inexpensive construction so that it may be re-sterilized by gas or readily disposable after a single use. In addition, the fiber optic sleeve provides an advantage for the anterior segment surgeon because it provides focal illumination and capability for simultaneous laser application.

SUMMARY OF THE INVENTION

In brief, arrangements in accordance with the present invention comprise a fiber optic sleeve device particularly adapted to be installed on a phacoemulsification instrument so as to provide a focal light source at the point of surgery. The conventional phacoemulsification instrument for which the fiber optic sleeve of the present invention is adapted consists of a handpiece containing a magneto-strictive ultrasonic mechanism that activates a hollow, 1 mm titanium needle covered with a soft silicone sleeve. The needle is drive by the ultrasonic mechanism to vibrate forty thousand times per second longitudinally in the axis of the needle. The mechanical vibration transforms the patient's lens into an emulsion, hence the name "phacoemulsification". One such instrument is marketed by Mentor O&O, Inc., 3000 Longwater Drive, Norwell, Mass. 02061

As the cataract is dissected by the high frequency phacoemulsification probe, it is sucked into the hollow titanium needle. Since removal of intraocular fluid must be balanced with the introduction into the eye with an equivalent amount of fluid, an irrigating solution is passed between the silicone sleeve and outer wall of the titanium needle. The silicone sleeve presently in use serves only as a conduit to direct flow of saline solution.

The present invention involves the incorporation of a specially designed fiber optic sleeve that substitutes for the presently used silicone sleeve. Thus, the fiber optic sleeve of the present invention provides for the transmission of the irrigating solution to the site of the cataract while also transmitting focal light to the point of surgery.

BRIEF DESCRIPTION OF THE DRAWINGS

A better understanding of the present invention may be realized from a consideration of the following detailed description, taken in conjunction with the accompanying drawing, in which:

FIG. 1 is a general schematic view showing a human eye in the process of undergoing a surgical procedure;

FIG. 2 is an enlarged schematic cross-sectional view showing a fiber optic sleeve and phacoemulsification instrument combination of the invention as used in the removal of a cataract from a human eye;

FIG. 3 is an enlarged schematic sectional view of the fiber optic sleeve of FIG. 2;

FIG. 3A is a schematic view, partially broken away, of a portion of the fiber optic sleeve of FIG. 3 showing one particular coupling arrangement;

FIG. 3B is a schematic view, partially broken away, of an alternative arrangement to that of FIG. 3A;

FIGS. 4A and 4B show alternative termination elements for use with the arrangement of FIG. 4;

FIG. 7 is a cross sectional view in axial section showing optical fibers linking the fiber optic sleeve with a source of radiation, the optical fibers being integrated with the device;

FIG. 8 is a cross sectional view in axial section showing a fiber optic bundle fed to the fiber optic sleeve through a centrally disposed aspiration channel and a peripherally disposed liquid infusion channel;

FIG. 8 A is a plan view of a support for a fiber optic bundle;

FIG. 9 is a cross sectional view in axial section showing another embodiment of a fiber optic bundle fed through a peripherally disposed liquid infusion channel;

FIG. 10 is an external view in side elevation showing a surgical handpiece employing the fiber optic sleeve used in conjunction with removal of cataract remnants by irrigation and aspiration;

FIG. 10 A is an external view in side elevation showing an enlarged portion of FIG. 10;

FIG. 11 is an external view in side elevation showing a surgical handpiece employing the fiber optic sleeve of this invention used in conjunction with irrigation during an anterior capsulotomy;

FIG. 12 is an external view in side elevation showing a surgical handpiece employing the fiber optic sleeve of this invention similar to that of FIG. 11 but used in conjunction with polishing the anterior surface of the posterior lens capsule; and, FIG. 13 is an external view in side elevation showing a surgical handpiece employing the fiber optic sleeve of this invention used in conjunction with a cyclodialysis cannula.

DETAILED DESCRIPTION OF THE PREFERRED EMBODIMENTS

Figure 5A:
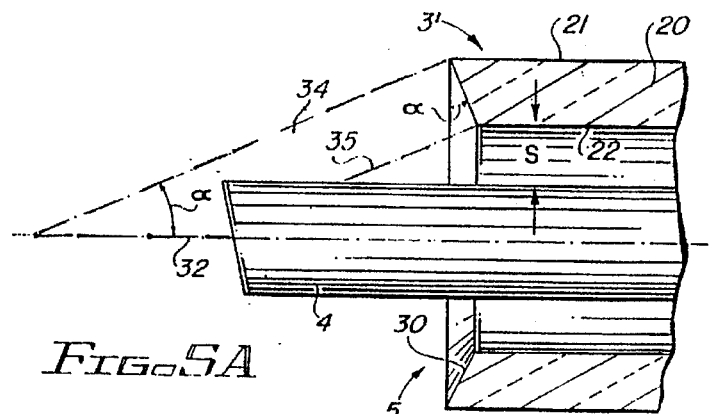
FIG. 5A is an enlarged schematic view of a portion of the embodiment of FIG. 5.

FIG. 1 shows a human eye in the process of undergoing a surgical procedure using a phacoemulsification-instrument 1 of conventional type with a sleeve 1A and needle 2. The instrument 1 is inserted through a scleral flap eye incision A and into the anterior chamber B.

FIG. 2 schematically represents a similar procedure being performed with the substitution of a fiber optic sleeve in accordance with the present invention. FIG. 2 shows an enlarged cross-sectional view of the eye. The cataract has been removed by conventional extracapsular surgical technique, including phacoemulsification, and the posterior capsule C remains intact. The fiber optic sleeve 3 is attached at the forefront of a phacoemulsification instrument 1. Optical fiber bundles 4 are shown extending from the sleeve 3. For the application disclosed, the fiber optic sleeve 3 is utilized for the purposes of endoillumination, video transmission, and application of photoablative laser energy to the pars plicata of the ciliary body for treatment of glaucoma.

FIG. 3 is an enlarged longitudinal schematic cross-sectional view of the present invention. The fiber optic sleeve has a proximal (leading) end 5 and a distal (trailing) end 6. With continuing reference to FIG. 3, the fiber optic assembly 3 consists of an elongated standard cannula adaptor 7 at the distal end 6 that is continuous with a frustoconical nipple 8, extending to cap 9, and then to a tapered applicator tip 10. An annular chamfer 11 and adjacent lipped flange 12 on the interior surface of the frustoconical nipple 8 permit insertion and securing of an internal coupler in the chamber 13 or for receiving an O-ring 14, which provides a liquid-tight seal when the sleeve is assembled on the surgical instrument. It is contemplated that other types of securing means such as locking rings can be used to secure the fiber optic sleeve member to the forefront of a surgical instrument. A circumferential lip 27 is provided at the distal end for facilitating installation of the sleeve 3 on a surgical instrument in preparation for use. The entire longitudinal length of the fiber optic sleeve 3 is approximately one inch.

The fiber optic sleeve 3 of the present invention is constructed of soft plastic material containing one or multiple fiber optic bundles. A fiber bundle 15 is shown in FIG. 3A and FIG. 3B. Material used in construction consists of vinyl plastic or other commercially available non-toxic medical grade plastic. Fiber optic bundles 15 contained within the body of the sleeve are constructed of commercially available quartz or zirconium fluoride optical fibers. The size of the central cylindrical bore 16 can be controlled during the manufacturing process, so that the fiber optic sleeve may be adaptable to a variety of surgical instruments. One or two portals 29 at the proximal end of the sleeve can be constructed at the time of manufacture to allow for flow of fluid between the fiber optic sleeve and the surgical instrument contained in its bore. Fluid entry allows maintenance of globe pressure and prevents excess heating of the laser element.

The cap 9, nipple 8 and cannula adaptor 7 are preferably encased by opaque silicone, tetrafluorethylene coating, or polyethylene cladding, which enhances optical transmission and also forms a protective sheath. The extent of cladding can be varied depending on the amount and direction of light transmission desired; cladding that terminates one millimeter from the proximal end of the applicator tip 10 would provide diffuse illumination, whereas cladding to the most anterior edge of the applicator tip 10 may be desirable in situations where a more focused beam is necessary. The face 18 of the proximal tip 10 is unclad and unencapsulated to provide uninterrupted application of light for illumination, microendoscopy, or laser beam application.

coupling to standard sources for video, illumination or video is secured at the distal portion of the fiber optic sleeve 3 by standard methods. Optical fiber couplers are well known in the prior art, for example see U.S. Pat. No. 4,089,584 of Christopher E. Polczynski. In FIG. 3 a recessed, female receptor well 19 at the distal face of the cannula adaptor 7 serves to connect to an external male fiber optic cable (not shown). Details of alternative embodiments are shown in FIGS. 3A and 3B. The embodiment of FIG. 3A comprises an internally threaded annular female well 19A having an accurately machined surface of revolution to interfit with a corresponding threaded male connector fiber optic source (not shown). The flat base of the receptor well 19A allows for a secure fit and good light transmitting connection between the fiber optic bundle from the light source and the optical fibers 15 in the sleeve 3. The number and placement of individual optical fibers arranged in receptacles in the receptor well 19 can be controlled during the manufacturing process.

Alternatively, the receptacle well of FIG. 3B is shown as a threadless cone 19B having a gradual internal taper for receiving a similarly tapered, mating end of the fiber optic cable from the light source [to an annular diameter smaller than the connecting fiber optic source]. In this arrangement, an external fiber optic cable is precision formed to mate snugly within the receptacle well 19B. In addition, the posterior end 6 can be attached to a laser catheter assembly by means of a conventional coupler or heat shrink wrap.

Figure 4:
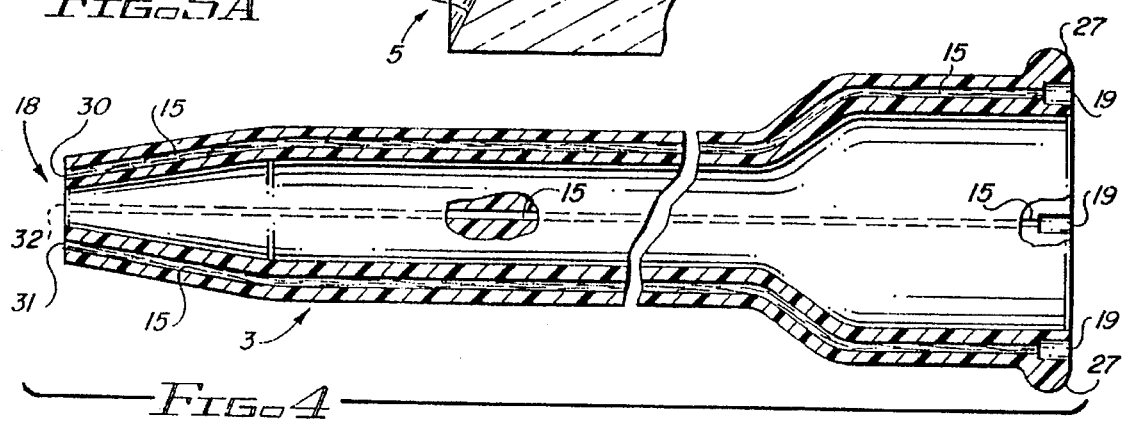
FIG. 4 is a schematic sectional view of an alternative embodiment of the invention.

FIG. 4 shows a tangential cross-sectional representation of the present invention. The fiber optic sleeve 3 consists of individual tracts of fiber optic bundles 15 of 500 to 600 micron quartz fibers having a bend radius of 4 centimeters or less that are incorporated within the body of the sleeve 3. The fiber optic bundles 15 within the sleeve 3 can be arranged in distinct radially-spaced coherent light conducting portions, or in fiber bundles having spatial fiber distribution. In accordance with one particular feature of the invention, the tips of the optical fibers within the bore of the sleeve are recessed slightly for providing a collimated output beam. It is contemplated that a lens such as the lens 28 of FIG. 4A can be fused at the proximal end of the fiber optic bundle for focusing laser energy 30, or at the proximal end of the fiber optic bundle for illumination 31, or at the proximal end of the fiber optic bundle for endoscopy 32. Alternatively, an end piece 33 bearing a plurality of lenses 28 for the respective bundles 15 at their respective terminations 30, 31 and 32 can be installed at the end face 18 of the sleeve 3. Such a lens may be manufactured with a combination of convex, concave or flat surfaces. In the example of FIG. 4A, a plano-concave lens is shown.

Figure 5:
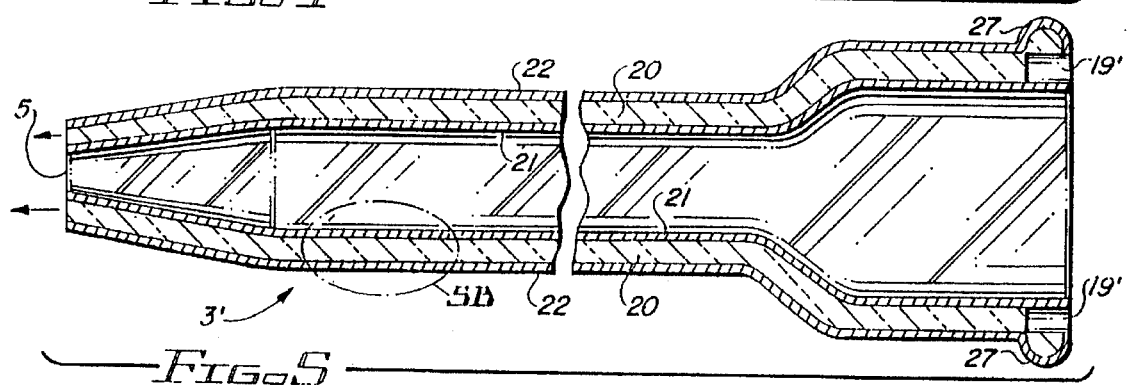
FIG. 5 is a schematic sectional view of still another embodiment of the invention.
Figure 5B:
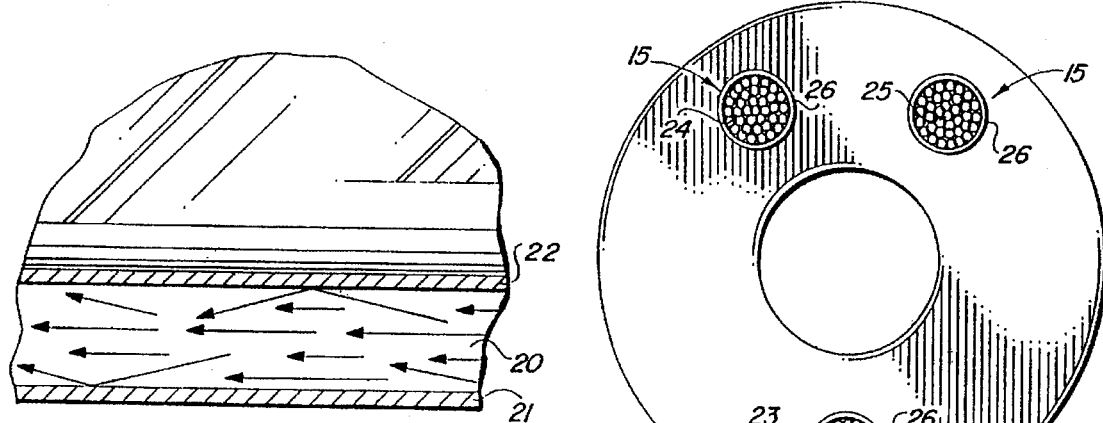
FIG. 5B is a cross sectional view in side elevation showing the enlarged portion 5B, which is indicated in FIG. 5; and, FIG. 6 is an enlarged schematic cross-sectional view showing details of the embodiment of FIG. 4.

FIG. 5 shows an alternative embodiment of the present invention consisting of a sleeve 3' of optically clear flexible plastic 20 encased on its outer 21 and inner 22 surfaces by a thin layer of silicone cladding or opaque, non-toxic plastic capsule with a low index of refraction, or by a reflective coating, such as polyetrafluorethylene, which enhances the optical transmission of the fiber optic sleeve. In this embodiment, the fiber optic bundles 15 are omitted because the entire sleeve 3' serves as an optical waveguide. The couplers 19', of which two are shown, are regularly spaced about the periphery and serve to couple the fiber optic bundles from a light source (not shown) into the optically clear plastic 20 for transmission of light to the tip end 5. Alternatively a diffusing collar may be provided, interposed between the light cable(s) and the sleeve 3'.

Preferably, the end face at the tip end 5 of the sleeve 3' should be beveled or angled inwardly so that the light emanating from the end face is directed at an angle radially inward toward the centerline of the embodiment. This is represented schematically in the enlarged schematic view of FIG. 5A which shows the end of the sleeve 3' encompassing a needle 4 and having a beveled end surface 30 extending at an angle $\alpha$ to a plane normal to the needle 40 The central axis of the needle 4 is represented by the broken line 32. The conical beam of light emanating from the beveled surface 30 is represented by the dashed lines 34, 35. The dashed line 34 intersects the axis line 32 at the same angle α. The inner surface 22 of the sleeve 3' is spaced from the needle 4 by a dimension s.

In practice, the angle α is a function of the dimensions of the needle 4 and the sleeve 3'. For a needle 4 having a diameter of 1 mm and projecting from the end 5 of the sleeve 3' by 2 mm, with sleeve wall thickness equal to 0.5 mm and spacing S also equal to 0.5 mm, the angle α should be approximately 23 degrees. If the spacing. S is reduced to 0.25 mm, the angle α should be slightly less than 20 degrees. Angle α can actually be calculated by determining its tangent: i.e., the distance from the outer surface of the sleeve 3' to the centerline 32 divided by the distance from the end 5 to the intersection of the light cone line 34 with the centerline 32. In such an arrangement, the light cone illuminates the field of view for approximately 1.5 mm beyond the needle tip and approximately 0.75 mm of the end of the needle 4.

Figure 6:
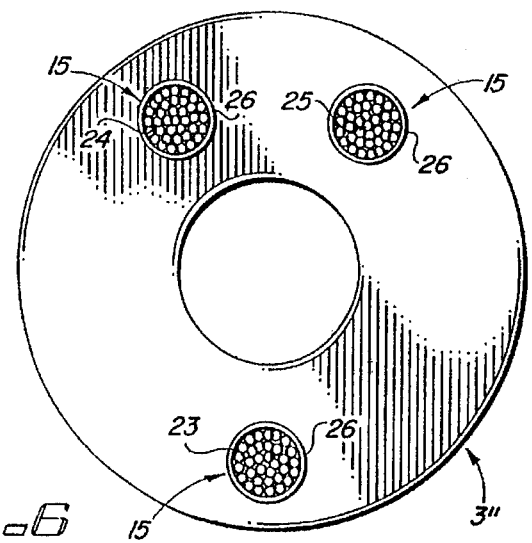

FIG. 6 illustrates an alternative embodiment of the fiber optic sleeve 3" that incorporates multiple bundle groups of optically segregated fibers for purposes of illumination 23, laser delivery 24, and microendoscopy 25 contained within the body of the sleeve. Segregated optical fiber bundle groups are coupled at the distal end to conventional delivery systems for illumination, laser delivery and microendoscopy for video broadcast. It will be understood that the optical fibers in the bundle-for microendoscopy must be maintained in the same orientation throughout their length in order that the pixel juxtaposition of the display will accurately represent the optical field of view. Optical segregation is accomplished by encapsulation of optic fiber bundles by optically opaque cladding 26 identical to that used on the external and internal surfaces of the sleeve 3' in the embodiment of FIG. 5.

Operation in Use.

The operation of the system is as follows:

A light cable, laser cable or video cable (not shown) is connected at a receptacle well 19 situated in the terminal rim 27 of the fiber optic sleeve 3. A fiber optic bundle conducts light between the attachment at the receptacle well 19, through the wall of the fiber optic sleeve cannula 7, cap 8, cap 9 and proximal face of the fiber optic applicator tip 10. Fiber optic bundles 15 terminating at the proximal face of the fiber optic sleeve 3 provide light to illuminate the operative area of regard, or may provide laser energy for treatment of intraocular structures. Separate and coherent fiber optic bundles 25 similarly coursing within the walls of the fiber optic sleeve, provide intraocular endoscopy. Saline fluid to maintain globe pressure enters from the contained surgical instrument and travels within the hypodermic lumen to be discharged at the open applicator tip 16 or portals 29 of the fiber optic sleeve. Operation is the same for illumination using the sleeve 3' of FIG. 5 by coupling the light cable directly to the sleeve 3'.

Although there have been described hereinabove various specific arrangements of a fiber optic sleeve for surgical instruments in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

In addition to using the fiber optic sleeve as an optical wave guide, as shown in FIGS. 1–6, optical fibers also can be incorporated in a phacoemulsification instrument for illumination, endoscopy and laser treatment, as shown in FIGS. 7–13 to produce an oblique illumination of the retina. These optical fiber components can be inserted through a vibrating needle; along a longitudinal axis between the central barrel and instrument casing; centrally into the instrument body by means of a connecting electrical power cable; through fluid irrigation and aspiration channels; through the connector coupling with the working vibrating needle or fiber optic sleeve; transmission through an accessory irrigation-aspiration handpiece; and transmission through an accessory cystotome or cannula.

Oblique lighting, provided by optical fibers integrated with phacoemulsification instrumentation provides decided advantages for the patient and operating surgeon. In the present state of the art, illumination of the surgical site is provided by direct coaxial illumination from an operating microscope. Direct and intense light from this source is associated with retinal phototoxicity and impaired vision. Thus, focal illumination from optical fibers integrated with phacoemulsification instruments are directed obliquely away from the retina, since the instruments are directed from a side incision. Illumination provided in this manner allows the operating surgeon to reduce the amount of direct light necessary to perform ocular surgery, which in turn minimizes the potential for retinal phototoxicity. In addition, visibility of intraocular structures is enhanced. The need for oblique lighting is further confirmed by a Public Health Advisory issued by the Food and Drug Administration (FDA) on Oct. 16, 1995 and incorporated herein by reference.

The intent of the FDA Public Health Advisory is to remind and caution ophthalmic surgeons of the "... retinal hazards from operating microscopes... and recommends actions to minimize the risk of retinal photic injury from operating microscopes...". The FDA Public Health Advisory recommends that ophthalmic surgeons "... use oblique lighting if it is available... to reduce risk of retinal photic injury."

Hence, the present invention combines a phacoemulsification instrument for cataract surgery using integrated optical fibers to produce lighting at an oblique angle to the retina. A suitable device for effecting the objects of this invention is shown in FIG. 7. The phacoemulsification device 39 of this invention comprises a hand held, elongate casing 40 defining a distal end 41 and a proximal end 42. An inlet port 43, connecting channel 43a and outlet port 43b enable infusion of fluid between an infusion sleeve and a working, vibrating needle to intraocular structures during surgery.

Mounted within the casing 40 is an acoustic transformer comprising a coupling member 44 bolted to the casing and connected or abutting a metallic coupling 45 such as stainless steel or titanium. Elastomeric O-rings 46, 47 form a water tight seal between the coupling member 44 and the casing 40 during fluid infusion through inlet port 43. A magnetostrictive or piezoelectric transducer 50 is mounted on the metallic coupling 45 and is actuated by current through an electric coil 51 which is supplied by current through a power cable 52 secured in distal end 41. Actuation of the transducer produces high frequency longitudinal vibrations which are transmitted to a hollow, titanium, plastic or ceramic needle 48 defining a working needle tip 48a and a needle base 48b, the needle being threadably mounted on the metallic coupling 45. Vibration of the hollow needle disintegrates tissue which contacts the working needle tip.

A coincident aspiration channel 53 extends from the channels 54 and 55 of the coupling member 44 and the metallic coupling 45, respectively. Tissue disintegrated by the working needle tip 48a at the surgical site is removed by aspiration through the needle 48 to the aspiration channel 53 using suction means (not shown) provided at the distal end 41 of the device 39.

A protective, non-toxic plastic infusion sleeve 57 for the needle 48 is mounted on the casing 40, and an annular space 58 is formed between the sleeve and the needle. Fluid infusion from the inlet port 43 passes through the annular space 58 to irrigate the surgery site and cool the vibrating needle. The working needle tip 48a extends slightly beyond the end of the infusion sleeve.

In one embodiment of the invention, a fiber optic bundle 60 containing one or more fiber optic lines enters the device 39 from its distal end, preferably in combination with the power cable 52. Alternatively, the fiber optic bundle 60 may be isolated from the power cable and enters the device at a separate port located at the distal end of the device. Also, the fiber optic bundle and electric power cable may supplied either by a common line or by separate lines into a single unit 61. The fiber optic bundle is threaded axially along the device, through the coupling 44 where it is secured, into the aspiration channel 53 at an angled inlet 63 adjacent to the base 48b of the needle 48, where it terminates. Rather than terminating at base 48b of the needle, the fiber optic bundle may extend partially or entirely through the needle. Alternatively, the proximal end of fiber optic bundle 60 may be coupled by standard means to the infusion sleeve 57 functioning as an optical wave guide, similar to FIG. 4. The aspiration channel 53 and inner surface of the needle may be machine polished or coated with a reflective coating such as TEFLON to enhance optical transmission.

Typically, the fiber optic bundle is encased in a protective jacket, and the surface of the jacket may be roughened or configured with protuberances to contact the inside wall of the casing 40 and minimize movement of the fiber optic bundle. If desired, the fiber optic bundle can be coated by a reflective material such as polyethylene, silicone, polytetrafluoroethylene (TEFLON), or a ceramic, to enhance reflectivity. A cone of light is formed at the proximal end of the fiber optic bundle which obliquely illuminates the retina similarly to FIG. 5A.

FIG. 8 is a schematic view of a fiber optic bundle fed through a central aspiration channel in addition to a fiber optic bundle on each side of the aspiration channel. The transducer components have been omitted for clarity.

The phacoemulsification device 63 in FIG. 8 provides a hand held, elongate, outer casing 64, infusion channel 65, aspiration channel 67, a hollow needle element 68 terminating the end of the channel 67, outer fiber optic lines 69 and 70 mounted within the outer casing 64, and a central fiber optic line 71 leading through the central aspiration channel 67. The fiber optic lines 69 and 70 are supplied by an Injection Laser Diode (ILD) source 72 or Light Emitting Diodes (LED), mounted within the device, and powered through a cable 73 from an external power supply (not shown). Alternatively, the fiber optic lines 69, 70 may be supplied by an external source of light (not shown). The proximal ends of the fiber optic lines terminate in standard fiber optic couplers such as ferrules which are manufactured by AMP. Suitable materials for ferrules include plastic, stainless steel metal, and ceramics such as alumina oxide or zirconia oxide.

A Y-shaped plastic adaptor 75 (which may be disposable) is mounted at the distal end of the aspiration channel 67, one branch 76 of the adaptor being supplied with a fiber optic bundle which leads through the central fiber optic line 71, and the other branch 77 of the adaptor being used to aspirate fluid and tissue remnants. The bore size of the aspiration channel 67 can be controlled during manufacturing so that it may accommodate a wide variety of fiber optic bundle sizes.

Alternatively, the fiber optic bundle can be supported by a fenestrated spoke wheel 80, as shown in FIG. 8a. A rim portion 81 mounts a plurality of spokes 82 which terminate in an annular hub 83 through which are threaded fiber optic bundles. The rim portion 81 of the spoke wheel functions as a supporting strut secured along the inside wall of the aspiration channel. The fiber optic bundles can extend for a variable length through the aspiration channel as a free floating member, and the number of spoke wheels employed depends on the extension length of the fiber optic bundles within the channel.

FIG. 9 shows an alternative embodiment of a phacoemulsification device 90, the transducer components being omitted for purposes of simplification. The device 90 comprises a hand held, elongate casing 91, a central aspirating channel 92, an infusion channel 93, and a hollow needle 94 mounted at the end of the aspirating channel. A light source for the device 90 is threaded through the distal end of the device and can be diverted into a plurality of isolated fiber optic bundles by means of a standard fiber optic star, or tree coupler 95. A plurality of optic bundles, two bundles 96, 97 being shown, are mounted within the casing 91 and terminate in connecting ferrules 98 and 99, respectively.

In addition to using fiber optic illumination by means of a phacoemulsification device illustrated in FIGS. 7–9, to produce oblique illumination, fiber optic bundles can be integrated with accessory cataract surgery instruments, as shown in FIGS. 10–13. FIG. 10 shows an irrigation-aspiration hand piece used for removal of cortical cataract remnants following removal of the cataract nucleus by phacoemulsification. The irrigation and aspiration tubing lines are connected to the irrigation-aspiration hand piece.

Typical devices, one of which is shown in FIG. 10 are sold by Alcon Surgical having trademark names SERIES 8000 I/A HANDPIECE and ULTRAFLOW I/A HANDPIECE. These Alcon Surgical products are described in their brochure numbered 905-2000-502, which is incorporated herein, by reference.

In FIG. 10, a hollow, cataract surgical handpiece 100 (SERIES 8000 I/A HANDPIECE) with channels for aspiration and irrigation provides a distal end 101 with ports 102 and 103 which connect with non-toxic plastic tubing to an irrigation fluid supply and a fluid aspiration pump (not illustrated) shown in the directions of the arrows. The proximal end 104 of the hand piece mounts an irrigation-aspiration tip 105 connected to the handpiece 100 at its base 106. The tip is used to remove cataract remnants by aspiration while maintaining intraocular pressure by irrigation. Fiber optic bundles are mounted through the irrigation supply port 102 and through the core of the handpiece body. Alternatively, the optic bundles may be mounted through the open distal end 101. As shown in the enlargement of FIG. 10a, a plurality of fiber optic bundles, two bundles 107 and 108 being shown, are mounted along the periphery of the base 106. Optic fiber couplers 109 and 110 connect the proximal ends of the fiber optic bundles to a light transmitting plastic infusion sleeve (not shown) similarly to preceding examples.

FIG. 11 illustrates a view of a hollow, cataract surgical hand piece 115 for supplying irrigation only, and onto which is mounted a cystotome 116 constructed of a light conducting material such as a plastic or a ceramic. This hand piece is used by the surgeon to perform an anterior capsulotomy after the entry incision is constructed. The irrigation hand piece is utilized to control the cystotome and deliver fluid to maintain intraocular pressure.

Fiber optic bundles, two bundles 119, 120 being shown, are incorporated in the irrigation hand piece in a similar manner to the irrigation-aspiration hand piece previously described. The fiber optic bundles terminate at the proximal tip 118 of the handpiece to couple with the plastic cystotome 116 and obliquely illuminate the retina. In this embodiment, optical fiber couplers 121 and 122 connect to recessed female receptor wells (not shown) at the distal face of the cystotome.

FIG. 12 illustrates a hollow, irrigation handpiece 130 of the same type as the hand piece 115 for supplying irrigation only, and to which is attached an irrigating scraping tip 131 that is similarly constructed of a light conducting material such as a plastic or ceramic. This instrument is used to polish the anterior surface of the posterior lens capsule. The distal end base 132 of the scraping tip 131 is connected to a plurality of fiber optic bundles, two bundles 133 and 134 being shown. Optical fiber couplers 135 and 136 function to transmit light to the irrigating scraping tip 131.

FIG. 13 illustrates a hollow, irrigating handpiece 140 similar to the hand pieces 115 and 130, and similarly constructed, and to which is attached a cyclodialysis cannula 141. The cyclodialysis cannula is used by the operating surgeon to sever intraocular tissue adhesions and manipulate the position of the intraocular lens. The distal end base 142 of the cannula is connected to a plurality of fiber optic bundles, two bundles 143 and 144 being shown. Optical couplers 145 and 146 connect the fiber optic bundles to the distal end of the cyclodialysis cannula.

It will be appreciated that a fiber optic bundle can extend either partly or completely through the accessory instruments 116, 131 and 141, instead of terminating at their respective bases, to produce oblique illumination of the retina.

I claim:

1. A disposable light transmitting sleeve, for use with a surgical instrument, comprising:
    a generally tubular structure shaped for attachment to a surgical instrument and formed of a soft, flexible, nontoxic medical grade plastic; and,
    means for controlling and directing optical radiation internally and substantially along the length of the sleeve.

2. A phacoemulsification instrument and disposable fiber optic sleeve comprising, in combination:
    a.) a phacoemulsification instrument having a hollow needle tip mounted in the forward end of the instrument;
    b.) a disposable light transmitting sleeve mounted on the forward end of the instrument and extending about said needle to near the terminal end thereof;
    c.) said sleeve being in the form of a generally tubular structure removably mounted on said surgical instrument and formed of soft, flexible, non-toxic medical grade plastic; and,
    d.) further including means for controlling and directing optical radiation internally of the sleeve and substantially along the length thereof for illuminating the terminal end of said needle.

3. A surgical instrument comprising in combination:
    a.) a phacoemulsification instrument having a forward end with a hollow needle mounted therein;
    b.) a disposable light transmitting sleeve mounted on the forward end of said instrument and extending about said needle to near the tip thereof, said tip comprising:
    c.) a generally cylindrical body of soft medical grade plastic material in the form of a shell extending about a hollow interior;
    d.) the interior of said body having means for engaging the terminal end of said surgical instrument;
    e.) said body having a proximal end and a distal end, the distal end being larger in diameter than the proximal end and sized to fit the terminal end of said surgical end of said surgical instrument;
    f.) a plurality of optical fibers extending within the shell between the distal and proximal ends for conducting optical radiation to illuminate a surgical field adjacent the proximal end; and,
    g.) means at the distal end for coupling the optical fibers to an external source of optical radiation.

4. A disposable light transmitting sleeve device for use with surgical instruments for endoscopy and the treatment of intracorporeal structures with optical radiation, comprising:
    a.) a sleeve formed of flexible, non-toxic medical grade plastic bounded by inner and outer wall surfaces and having a hollow lumen shaped and sized to fit the forefront of a surgical instrument on which the sleeve is to be mounted, the sleeve having a proximal end to be located adjacent the terminal end of the surgical instrument and a distal end remote from said proximal end, the distal end being larger in diameter than the proximal end;
    b.) coupling means for removably mounting the sleeve on the forefront of a surgical instrument; and,
    c.) light transmitting means mounted within the plastic material of said sleeve and extending from the distal end to the proximal end in order to transmit optical radiation the length of said sleeve within said plastic between said surfaces.

5. A phacoemulsification device for oblique illumination of a retina field, comprising:
    a.) a hollow body hand piece portion comprising port and channel means including a proximal inlet infusion port, a connecting infusion channel, a distal outlet aspiration port and a connecting aspiration channel;
    b.) a working end piece mounted proximally of the device and defining a hollow portion, a base portion, and a working tip; and,
    c.) a fiber optic bundle mounted within the hand piece and secured therein;
    d.) means to provide illumination radiation to the fiber optic bundle; and,
    e.) means to couple radiation output from the fiber optic bundle to illuminate an area adjacent to, and including the hollow portion of the working end piece, thereby obliquely illuminating a surgical field within the area, and including the working tip of the end piece.

6. The device of claim 5, in which the fiber optic bundle is disposed within the infusion channel.

7. The phacoemulsification device of claim 5, in which the fiber optic bundle is disposed within the aspiration channel.

8. The phacoemulsification device of claim 5, in which the fiber optic bundle is disposed within the infusion channel and the aspiration channel.

9. The phacoemulsification device of claim 5, in which the end piece includes one of: a cannula, an irrigation device, an irrigation-aspiration device, a light transmitting infusion sleeve and a working, vibrating needle.

10. The phacoemulsification device of claim 9, in which the cannula consists of a cyclodialysis cannula and a cystotome cannula.

11. The phacoemulsification device of claim 5, in which the channels are coated with a reflective coating to improve radiation transmission from a fiber optic bundle.

12. The phacoemulsification device of claim 5, in which the end piece is coated with a reflective coating to improve radiation transmission from the fiber optic bundle.

13. The phacoemulsification device of claim 5, in which the working end piece comprises a vibrating needle, and power for the vibrating needle and power for the fiber optic bundle are formed into a combined cable.

14. The phacoemulsification device of claim 5, in comprising a vibrating needle working end piece, and a single unit for supplying power to the vibrating needle and radiation for the fiber optic bundle.

15. The device of claim 5, comprising means to secure the fiber optic bundle within the hand piece.

16. The device of claim 15, providing an optical coupler including tree and star coupler means to for the fiber optic bundle.

17. The device of claim 5, comprising radiation producing means disposed within the hand piece.

18. The phacoemulsification device of claim 5, in which the port and channel means comprises an inlet port and an infusion channel.

19. The phacoemulsification device of claim 5, in which the fiber optic bundle terminates at the base of the device.

20. The phacoemulsification device of claim 5, in which the fiber optic bundle extends into the working end piece.

21. The phacoemulsification device of claim 5, comprising a Y-connector mounted at the distal port of the device for mounting the fiber optic bundle and the distal aspiration channel.

22. The phacoemulsification device of claim 5, comprising strut means to support the fiber optic bundle within the device.

* * * * *